United States Patent [19]

Sawai et al.

[11] Patent Number: 5,376,637

[45] Date of Patent: Dec. 27, 1994

[54] PHARMACEUTICAL PREPARATION CONTAINING VASOACTIVE INTESTINAL POLYPEPTIDE OR ITS ANALOGUE

[75] Inventors: Kiichi Sawai; Masayasu Kurono; Takahiko Mitani; Makoto Sato; Haruo Takahashi; Hiroyuki Ohwaki, all of Nagoya, Japan

[73] Assignee: Sanwa Kagaku Kenkyusho Co., Ltd., Aichi, Japan

[21] Appl. No.: 868,906

[22] Filed: Apr. 16, 1992

[30] Foreign Application Priority Data

Apr. 22, 1991 [JP] Japan .................. 3-090671

[51] Int. Cl.⁵ ............... A61K 37/00; A61K 37/02; C07K 5/00; C07K 7/00
[52] U.S. Cl. .......................... 514/12; 514/13; 514/14; 514/15; 514/16; 530/324; 530/327; 530/328
[58] Field of Search ............... 514/12, 13, 14, 15, 514/16; 530/324, 327, 328

[56] References Cited

U.S. PATENT DOCUMENTS 4,737,487  4/1988  Watts et al. ............... 514/15
4,866,039  9/1989  Wootton et al. ........... 514/16

FOREIGN PATENT DOCUMENTS 56-128721  10/1981  Japan .
62-16429   1/1987   Japan .
16429(A)   1/1987   Japan .
62-116595  5/1987   Japan .
62-246595  10/1987  Japan .
63-179892  7/1988   Japan .
64-83012   3/1989   Japan .
1-83012(A) 3/1989   Japan .
1-296996   11/1989  Japan .
053754545  3/1990   Japan .

OTHER PUBLICATIONS

Peptides, vol. 6, pp. 597–601, 1985.
Microbiol. Immunol., vol. 22, pp. 89–101, 1978.

*Primary Examiner*—Lester L. Lee
*Assistant Examiner*—A. M. Davenport
*Attorney, Agent, or Firm*—Nikaido, Marmelstein, Murray & Oram

[57] ABSTRACT

There is disclosed a pharmaceutical preparation which contains vasoactive intestinal polypeptide (VIP), its analogue or a salt thereof, and a surfactant. The preparation shall contains further a peptidase inhibitor. The composition is administered to suppress allergies, reduce blood pressure, increase secretion of tear, cure asthma and impotence and others.

8 Claims, 3 Drawing Sheets

↓ : Add Histamine ( $10^{-5}$ M )

⇓ : Add [L-Leu$^{17}$]-VIP-Hse ($10^{-7}$ M)

↓ : Add Histamine ($10^{-5}$ M)

↓ : Add native type VIP ($10^{-7}$ M)

↓ : Add Histamine ($10^{-5}$M)

⇓ : Add [L-Leu$^{17}$]-VIP-Hse ($10^{-8}$M)

↓ : Add Histamine ($10^{-5}$M)

⇣ : Add native type VIP ($10^{-8}$M)

PHARMACEUTICAL PREPARATION CONTAINING VASOACTIVE INTESTINAL POLYPEPTIDE OR ITS ANALOGUE

BACKGROUND OF THE INVENTION

1. Field of the Invention

The present invention relates to a pharmaceutical preparation containing a vasoactive intestinal polypeptide (hereinafter referred to as "VIP") or its analogue and more particularly, to a preparation excellent in absorptiveness.

2. Related Arts

The VIP is one of the peptide hormones and was first isolated and refined by Said and Mutt in the year of 1970 from a subfraction, when secretin was extracted from a tissue of porcine upper small intestine. In 1974, a primary amino acid structure of the VIP was made apparent as consisting of 28 amino acids and it has been considered that it belongs to a glucagon-secretin family.

Amino acid sequence of the native VIP (SEQ ID NO: 1)

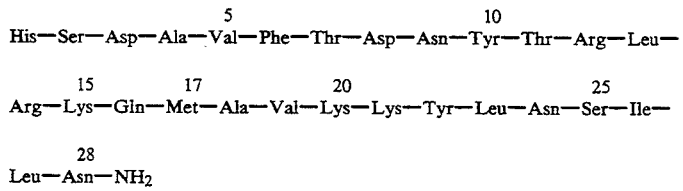

It has been confirmed that the VIP is present in nervous systems in addition to the digestive canal to develop various biological activities, for instance a relatively high vasodilating-hypotensing action; atonic action on smooth muscle; accelerating action of intestinal juice secretion, pancreatic juice and bile secretions, and tear secretion; suppressing action of gastric juice secretion; accelerating action of glycogen decomposition; accelerating action of various pituitary hormone secretions; increasing action of blood flow into penis; vasodilating action of bronchus; anti-allergic action; anti-tumor action; growing action of hair, and so on.

Following patent literatures have been issued in Japan on the VIP, VIP analogues and use thereof.
a) Jap. Pat. No. Sho 56 (Year of 1982)—128721(A), Anti-allergic agent;
b) Jap. Pat. No. Sho 62 (Year of 1987)—16429(A), Acceleration of tear secretion;
c) Jap. Pat. No. Sho 62 (Year of 1987)—116595(A), Anti-tumor and ulcer agent;
d) Jap. Pat. No. Sho 62 (Year of 1987)—246595(A), Bronchodilatation agent and hypotensor;
e) Jap. Pat. No. Sho 63 (Year of 1988)—179892(A), Acceleration of blood flow;
f) Jap. Pat. No. Sho 64 (Year of 1989)—83012(A), An agent for growing hairs;
g) Jap. Pat. No. Hei 1 (Year of 1989)—296996(A), Hypotensor; and
h) Jap. Pat. No. Hei 2 (Year of 1990)—76821(A), External preparation for curing impotence.

In view of those biological activities, the VIP has been expected as the drugs for curing asthma and impotence, by utilizing the bronchodilitating and atonic activities on smooth muscle of corpus cavernosum, respectively. A structural characteristic of the VIP lies in that there is an amide structure at the C-terminal, which has been estimated as an indispensable matter for developing the biological activities of VIP.

Hitherto, it has been considered as quite difficult to provide the VIP or VIP analogues with a reasonable price and in a large amount, since according to the prior arts, there is no way other than utilizing a synthetic process therefor or an extraction method thereof from an animal tissue, and the former requires troublesome operations due to that the VIP is polypeptide consisting of 28 amino acids, and takes a relatively long period of time in its chemical synthesis and for purifying the same, and the latter is restricted on availability of the raw material and requires troublesome purification procedures.

For obtaining a polypeptide having an amide structure at C-terminal as the VIP in accordance with conventional and widely accepted biological techniques which utilize an expression microorganism such as *Escherichia coli*, in general, it is required to separate and purify an expressed polypeptide and then to treat the polypeptide with use of a special C-terminal amidation enzyme. However, such an enzymatic method is not suitable for industrial scale production, since such enzyme is expensive and yield of the objective polypeptide becomes low.

It has also been reported that a chemically synthesized VIP analogue—methionine residue at 17th position of the native type VIP being substituted with leucine or norleucine—shows biological activities similar to the native type VIP [said Jap. Pat. No. Sho 62 (Year of 1987)—246595(A)]. Therefore, it has been considered that the methionine residue at 17th position has almost no influence on useful activities of the VIP.

The present inventors have energetically studied and investigated polypeptides obtained through a fermentation method or chemical synthesis and with a VIP-like structure to find out that a polypeptide represented by a following formula and obtained through the cleaving step using cyanogen bromide shows desired biological activities in same level or higher than native type VIP and [Leu17]-VIP, and that an amide or alkyl amine can easily be bound to the residue in accordance with a conventional synthetic method, to open a way for producing the VIP analogues in a large amount and with a reasonable cost [Jap. Pat. Appln. Nos. Hei 2 (Year of 1990)—165739 and 408425 which correspond to U.S. Ser. No. 07/704,143 and EP-0 463 450(A1) (SEQ ID NO: 2):

His-Ser-Asp-Ala-Val-Phe-Thr-Asp-Asn-Tyr-Thr-
Arg-Leu-Arg-Lys-Gln-X-Ala-Val-Lys-Lys-Tyr-
Leu-Asn-Ser-Ile-Leu-Asn-Y wherein X is a residue of amino acid other than methionine (Met); and Y is homoserine, homoserine-lactone, amidized homoserine, a residue reacted homoserine-lactone with a primary alkyl amine having carbon atoms not exceeding 20, or an optional polypeptide chain and containing an amidized homoserine at C-terminal.

In general, biologically active peptides are apt to be affected by external factors such as heat, humidity, light beam and peptidase. Therefore, the inventors have checked the stability thereof and groped for various methods for administration thereof for developing an actual medicine comprising the VIP analogue as an effective ingredient and found out that the VIP analogues are somewhat improved in stability than the native type VIP and [Leu$^{17}$]-VIP, but can not be said as having a sufficient stability. Namely, if the VIP analogue is dissolved in water to lyophilize the solution and the resulting powder is stored in a refrigerator and the powder is dissolved into saline or the like, when the time for administration by injection, a reduction of activity can be fairly suppressed, but the injection accompanies a pain to patients to restrict an application range, and in other administration methods such as oral dosage, suppository or the like, the VIP analogue is apt to be decomposed and lack a development of expected pharmacological activity.

SUMMARY OF THE INVENTION

An object of the invention is to provide a pharmaceutical preparation comprising native type VIP, its analogue or a pharmaceutically acceptable salt thereof, as an effective ingredient, which is excellent in absorptiveness.

According to the invention, the object can be attained by a pharmaceutical preparation comprising an effective amount of substance selected from the group consisting of native type VIP, its analogue and a pharmaceutically acceptable salt thereof, and a surfactant.

A absorptiveness of the preparation can be improved, when its further contains a peptidase inhibitor.

The invention aims to use, mainly, the VIP analogue shown by the formula of (SEQ ID NO: 2)

His-Ser-Asp-Ala-Val-Phe-Thr-Asp-Asn-Tyr-Thr-
Arg-Leu-Arg-Lys-Gln-X-Ala-Val-Lys-Lys-Tyr-
Leu-Asn-Ser-Ile-Leu-Asn-Y wherein X is a residue of amino acid other than methionine (Met); and Y is a homoserine, homoserine-lactone, amidized homoserine, a residue reacted homoserine-lactone with a primary alkyl amine having carbon atoms not exceeding 20, or an optional polypeptide chain and containing an amidized homoserine at C-terminal, since each of the analogues can be prepared in large amount with a reasonable cost by utilizing biotechnologies, as referred to before [Jap. Pat. Appln. Nos. Hei 2 (Year of 1990)—165739 and 408425 which correspond to U.S. Ser. No. 07/704143 and EP-0 463 450(A1)].

As the salt, those with an inorganic acid such as hydrochloric acid, bromic acid, sulfuric acid and phosphoric acid, or those with an organic acid such as citric acid, succinic acid, acetic acid, alkylcarbonic acid and ascorbic acid can be employed.

As the surfactant, followings can be listed, namely triterpene type, steroid and glycol higher ether type substances with a surface-activity; metal bilates (sodium deoxycohlate and the like); saponin; polyoxyethylene glycol higher alcohol ethers (polyoxyethylene lauryl ether and the like); and nonionic surfactants (polyoxyethylene sorbitan fatty acid ester, sucrose fatty acid ester and the like). A specific surfactant is selected by taking a kind of disease, a form of medicine, an estimated period of time for curing the disease and other factors into consideration. For a nasal drop, it is preferable to select one of sodium deoxycohlate, saponin and polyoxyethylene lauryl ether, in order to prevent side effects such as a congestion of mucous membrane in nose. It shall be estimated that the surfactant causes a dispersion of VIP or the like substance in suitable extent and dilatation in tissue to accelerate absorption of the substance.

As the peptidase inhibitor, followings can be listed, namely trypsin inhibitor; chymotrypsin inhibitor; gavexates; guanidinobenzoic acid; and acidic polysaccharides (sulfated dextran and the like).

A dosage of the substance (VIP, its analogue or a salt thereof) depends on various factors, for instance kind of the substance, kind and condition of the disease, age of a patient and form of the medicine, but in the case of an adult and selecting [L-Leu$^{17}$]-VIP-Hse, 0.1–10 mg is preferable as one dosage through a skin or mucous membrane in nose, and 1–100 mg is preferable as one dosage for other dosing routes. The pharmaceutical preparation according to the invention can be made into one showing an immediate or sustaining action by utilizing conventional medicine preparation techniques. For the preparation, a filler, binder, disintegrator, buffer, stabilizer, preservative, solubilizing agent, pH adjusting agent, isotonizer or the like can be used. There is no specific limitation in form of the preparation. For oral dosage, the preparation may take a form of solution, powder, tablet, capsule, buccal, troche or the like. A form of inhalation in liquid or powder, or suppository may be taken for narsal administration. An eye drop or ointment may be prepared for ophthalmic administration. A suppository can be selected for rectal administration. A form of ointment shall be selected for applying same for a penis. The ointment may also be applied on inner surface of a contraceptive sheath.

DETAILED DESCRIPTION OF PREFERRED EMBODIMENTS

Figure 1:
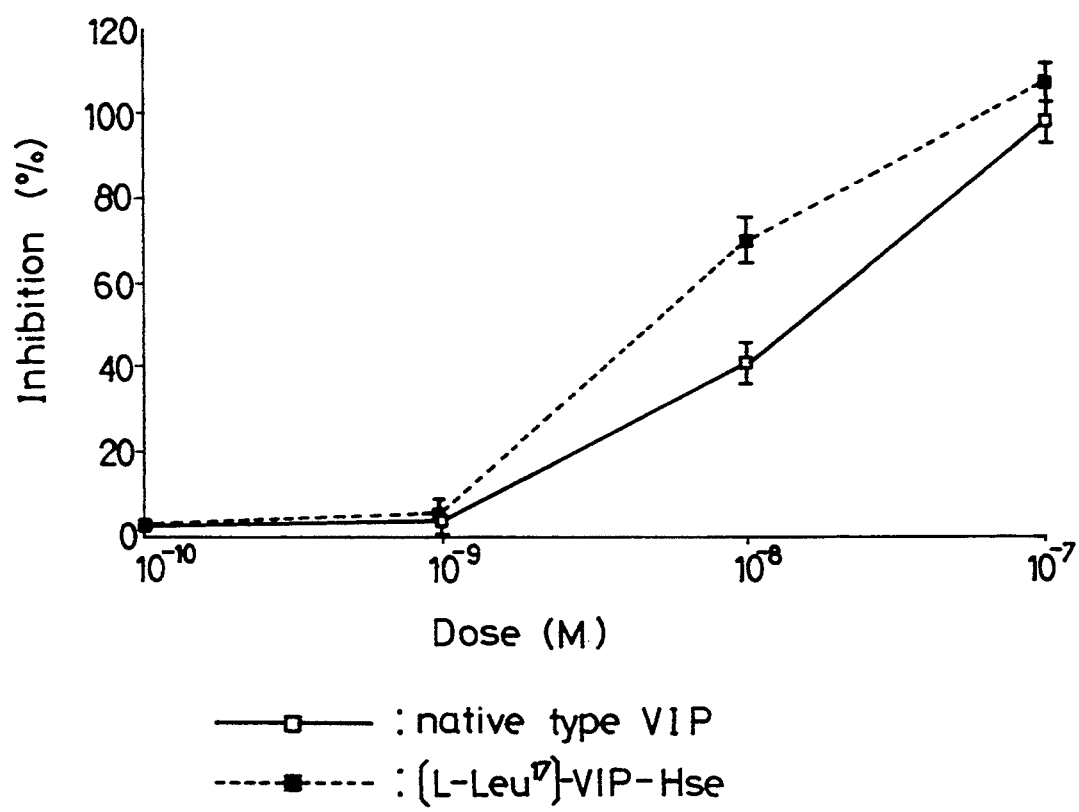
FIG. 1 is a graph showing results of measurements on reluxant activity in isolated guinea pig airway smooth muscle, in accordance with Magnus method, which relaxation is caused by [Leu$^{17}$]-VIP-Hse (test sample) and by a native type pure VIP (control sample) available from the market.

The invention will now be further explained in more detail with reference to Reference Example, Medicine Preparation Examples as well as Pharmacological Test Examples.

REFERENCE EXAMPLE a) Synthesis of [L-Leu$^{17}$]-VIP-Hse(lactone)

In the first place, a compound of Boc-Hse(Bzl)-4-(oxymethyl)phenylacetic acid was chemically synthesized. With use of the compound and commercially available amino methyl resin, [Leu$^{17}$]-VIP-Hse encoding following amino acid sequence was synthesized by utilizing a peptide synthesizer (Type 430A marketed by Applied Biosystems Co.) and subsequent treatment for removing protective radicals and resin (SEQ ID NO: 3)

His-Ser-Asp-Ala-Val-Phe-Thr-Asp-Asn-Tyr-Thr-
Arg-Leu-Arg-Lys-Gln-Leu-Ala-Val-Lys-Lys-
Tyr-Leu-Asn-Ser-Ile-Leu-Asn-Hse(lactone)

After treated with 0.5M ammonia solution in ice-bath for 30 minutes, a purification of the synthesized polypeptide was carried out by subjecting to HPLC with use of a μ bondasphere C-18 column (19 mm×15 cm) marketed by Waters Co, under following conditions.

Elute: Linear gradient of 15% to 50% acetonitrile in 0.1% trifluoroacetic acid (35 minutes),
Flow rate: 7.0 ml/min.

Fractions in a main peak part on the HPLC were recovered and lyophilized. Through said proceedings, the synthesized polypeptide encodes said amino acid sequence with homoserine or homoserine-lactone residue at C-terminal.

A part of the resulting VIP analogue was taken and checked with use of a peptide sequencer marketed by Applied Biosystems Co. to confirm that the synthesized polypeptide encodes the desired amino acid sequence inclusive of the homoserine or homoserine-lactone residue at C-terminal.

b) Synthesis of [L-Leu$^{17}$]-VIP-Hse-NH$_2$

The polypeptide with the homoserine(lactone) residue at C-terminal was collected through HPLC and lyophilized. The resulting dried powder was treated with 10% ammonia in dimethylformamide solution at room temperature for 24 hours to prepare a desired VIP analogue.

c) Synthesis of other VIP analogues

[L-Leu$^{17}$]-VIP-Hse-NH(CH$_2$)$_9$CH$_3$ and [L-Leu$^{17}$]-VIP-Hse-NH(CH$_2$)$_{19}$CH$_3$ were prepared by reacting the polypeptide with homoserine(lactone) residue at C-terminal with a primary alkyl amine of CH$_3$(CH$_2$)$_9$CH$_2$ or CH$_3$(CH$_2$)$_{19}$NH$_2$, in dimethylsulfoxide solution.

REFERENCE MEDICINE PREPARATION EXAMPLE (Injection)

A solution of the VIP analogue ([L-Leu$^{17}$]-VIP-Hse) in refined water was aseptically charged into vials, so that each vial contains the VIP analogue by 1 mg. After lyophilized, the vial was sealed to obtain a dry powdery medicine. The powdery medicine is dissolved in saline or the like for injection purpose, when it shall be used.

For stabilizing the VIP analogue, a human serum albumin or the like can be added.

Medicine Preparation Example 1 (Dry powder for nasal drop)

To an aqueous solution (5 ml) containing 3 mg of [L-Leu$^{17}$]-VIP-Hse-NH$_2$, were added sodium glycocohlate (30 mg) and mannitol (100 mg) to dissolve the same. The solution was lyophilized to obtain a dry powder. The powder is dissolved in refined water to prepare a nasal drop, when it shall be used.

MEDICINE PREPARATION EXAMPLE 2

(Powder for Nasal Administration)

To an aqueous solution (10 ml) containing 30 mg of native type VIP, were added poloxyethylene cetyl ether (20 mg) and human serum albumin (100 mg) to dissolve the same. The solution was spray dried and screened with a sieve of 100 mesh to obtain a powdery medicine for nasal administration.

MEDICINE PREPARATION EXAMPLE 3

(Powder for Nasal Administration)

To an aqueous solution (15 ml) containing 30 mg of [L-Leu$^{17}$]-VIP, were added poloxyethylene lauryl ether (25 mg) and human serum albumin (100 mg) to dissolve the same. The solution was spray dried and screened with a sieve of 100 mesh to obtain a powdery medicine for nasal administration.

MEDICINE PREPARATION EXAMPLE 4

(Solution for Nasal Administration)

To an aqueous solution (5 ml) containing 5 mg of [L-Leu$^{17}$]-VIP-Hse-NH(CH$_2$)CH$_3$, was added saponin (50 mg) to prepare a desired solution for nasal administration. The solution can be sprayed into nasal fossa or applied on mucous membrane therein.

MEDICINE PREPARATION EXAMPLE 5

(Hydrogel Type Medicine)

A hydrogel type medicine was prepared in a conventional manner and with a following prescription. The medicine was charged into an aluminum tube for packing the same.

| | |
|---|---|
| [L-Leu$^{17}$]-VIP-Hse-NH$_2$ | 300 (mg) |
| Hydroxypropylmethylcellulose | 100 |
| Polysorbate 60 (Note: Trademark) | 100 |
| Gelatin | 500 |
| 70% Aqueous solution of sorbitol | 2000 |
| Citric acid | 100 |
| Disodium hydrogenphosphate | 300 |
| Sodium chloride | 500 |
| Benzalkonium chloride | 20 |
| Refined water | remainder |
| Total | 100 (g) |

MEDICINE PREPARATION EXAMPLE 6

(Suppository for Nasal Administration)

A suppository (50 mg) for nasal administration, which contains 1 mg of [L-Leu$^{17}$]-VIP was prepared by mixing the powdery medicine obtained by Medicine Preparation Example 3 into a glycerogelatinic suppository base and molding the same.

MEDICINE PREPARATION EXAMPLE 7

(Granule)

To prepare a granular preparation of 1 g in dose for each time, [L-Leu$^{17}$]-VIP-Hse-NH$_2$. gavexate (10 mg) and sucrose palmitate (200 mg) were mixed. To the mixture, were added lactose, starch and hydroxypropylcelluose in each suitable amount to prepare granules in a conventional manner. Then, an enteric coating was applied thereto with use of hydroxypropylmethylcellulose (P).

MEDICINE PREPARATION EXAMPLE 8

(Tablet)

Tablets were prepared in a conventional manner and with a following prescription.

| | |
|---|---|
| [L-Leu$^{17}$]-VIP-Hse | 10 (mg) |

| -continued | |
|---|---|
| Sodium lauryl sulfate | 20 |
| Carboxymethylcellulose (Ca) | 7 |
| Crystalline cellulose | 2 |
| Magnesium stearate | 7 |
| Lactose | remainder |
| Total | 200 (mg)/tablet |

MEDICINE PREPARATION EXAMPLE 9

(Suppository)

Suppositories were prepared in a conventional manner and with a following prescription.

| | |
|---|---|
| [L-Leu$^{17}$]-VIP-Hse | 20 (mg) |
| Tannic acid | 30 |
| Ichthamol | 300 |
| Cacao butter | remainder |
| Total | 1000 (mg)/piece |

MEDICINE PREPARATION EXAMPLE 10

(Ointment)

An external cream or ointment was prepared in a conventional manner and with a following prescription.

| | |
|---|---|
| [L-Leu$^{17}$]-VIP-Hse-NH$_2$ | 100 (mg) |
| Tannic acid | 100 |
| White petrolatum | remainder |
| Total | 100 (g) |

This type medicine is applied directly on to penis or internal surface of a contraceptive sheath.

MEDICINE PREPARATION EXAMPLE 11

(Ophthalmic Solution)

An ophthalmic solution was prepared in a conventional manner and with a following prescription.

| | |
|---|---|
| [L-Leu$^{17}$]-VIP-Hse | 1000 (mg) |
| Sodium dihydrogenphosphate (anhydride) | 560 |
| Disodium hydrogenphosphate (anhydride) | 370 |
| Sodium chloride | 370 |
| Benzalkonium chloride solution (diluted to 1/50000) | remainder |
| Total | 100 (ml) |

BIOLOGICAL ACTIVITY TEST EXAMPLE 1

(Inhibition of Bronchus Contraction)

An inhibition of bronchus contraction was measured in accordance with a so-called "Magnus method" as disclosed in "Peptides", Vol. 6, pages 597–601 (1985) which uses an airway smooth muscle of guinea pig, on the VIP analogue of [L-Leu$^{17}$]-VIP-Hse, as Test Sample and a marketed native type pure VIP, as Control Sample [Each of the airway smooth muscles were toned with histamine (Conc.: 10$^{-5}$ M)].

Figure 2A:
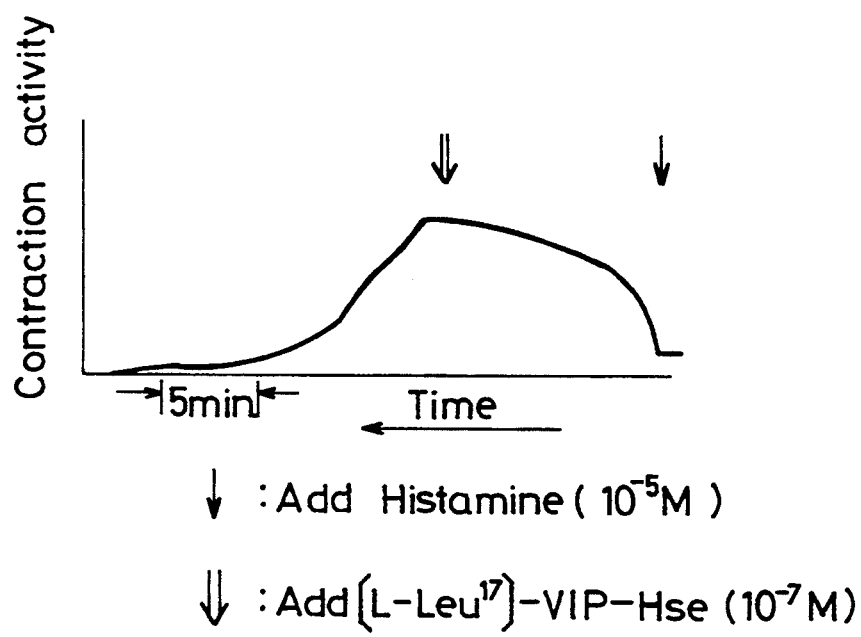
FIGS. 2A and 2B are, respectively, a chart showing details of that a bronchus contraction induced by histamine will be atonized by adding a test sample of [L-Leu$^{17}$]-VIP-Hse and control sample of native type pure VIP, in case of that concentration of each sample of $10^{-7}$ M.
Figure 2B:
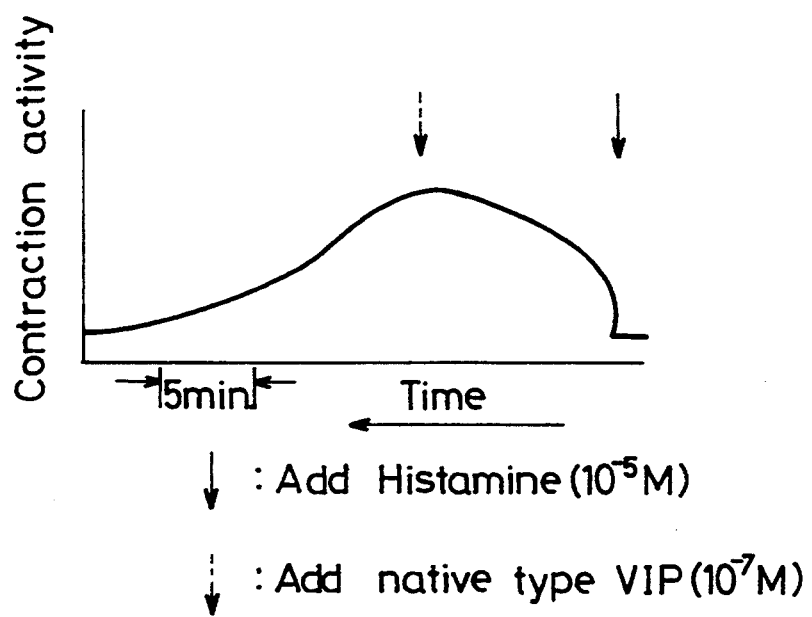
Figure 3A:
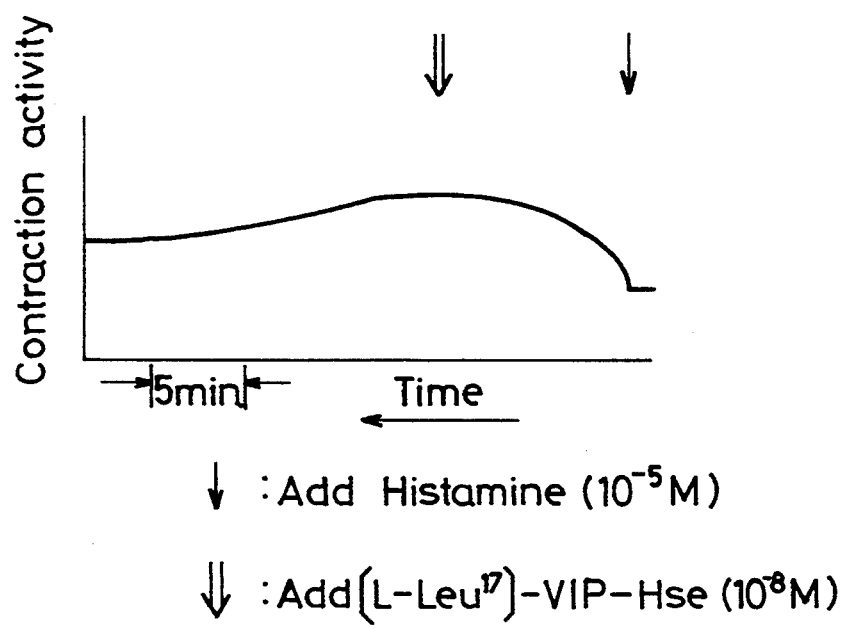
FIGS. 3A and 3B are, respectively, a chart similar to FIGS. 2A and 2B, but in case of that concentration of each sample is $10^{-8}$ M.
Figure 3B:
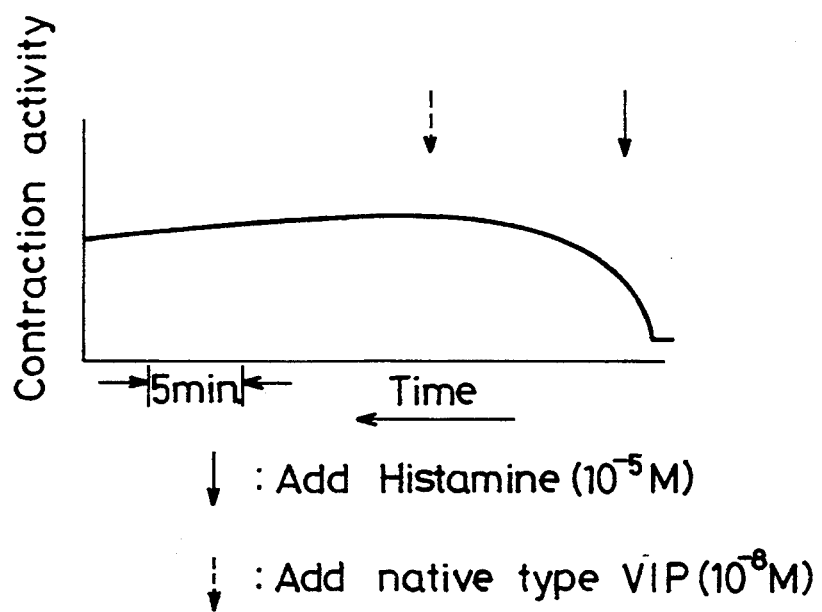

Results are shown in FIGS. 1–3. From the Figures, it is apparent that the VIP analogue shows the higher relaxative activity than that of the native type VIP.

PHARMACOLOGICAL TEST EXAMPLE 2

(Anti-allergic Action)

(1) Preparation of antiserum

A rat was immunized with egg-albumin suspended in aluminum hydroxide gel in a conventional manner and a blood letting was carried out to obtain an antiserum rich in IgE.

(2) Passive cutaneous anaphylaxis test (PCA reaction)

A male rat was anesthetized with ethyl ether and hairs on back were sheared to intradermally inject by 0.1 ml of the antiserum solution (diluted to 5-folds in volume) described in Item (1), at both sides with a certain distance from a medial line on the back. After 72 hours, a mixed solution of egg albumin (5 mg/kg), 2% Evans blue and a test compound (L-Leu$^{17}$]-VIP-Hse or pure native type VIP) or disodium cromoglycate was injected into a vein, under anesthetized with pentobarbital. After 30 minutes from an occasion of PCA reaction, the experimental animal was killed and pealed-off the skin to obtain a piece of the skin dyed with the coloring matter.

The coloring matter was extracted in accordance with the method described by Katayama ["Microbio. Immunol.", Vol. 22, No. 2, pages 89 (1987)] and an amount thereof was measured at 620 nm in wave length to calculate an inhibition of the PCA reaction.

Results are shown in following Table 1. From the Table, it is apparent that the VIP analogue shows the inhibition substantially equal to that of the native type VIP.

TABLE 1

| | Inhibition (%) | | |
|---|---|---|---|
| Dose (mg/kg) | A | B | C |
| 0.01 | 31 | 23 | 5 |
| 0.1 | 79 | 72 | 28 |
| 1.0 | 68 | 67 | 31 |

In the Table,
A : [L-Leu$^{17}$]-VIP-Hse;
B : Native type VIP; and
C : Disodium cromoglycate.

In the Table,
A: [L-Leu$^{17}$]-VIP-Hse;
B: Native type VIP; and
C: Disodium cromoglycate.

PHARMACOLOGICAL TEST EXAMPLE 3

(Hypotensing Action)

In a femoral artery of anesthetized beagle dog (body weight: about 10 kg), each of VIP analogues as Test Samples was injected in a dose of 0.02–10 μg/kg and measured an arterial pressure to prepare a chart showing a relation between the dose and change in blood pressure and check an amount of dose which shall cause a reduction of 15 mmHg in blood pressure.

Following Table 2 shows an effect of the VIP analogues with a relative value, when an amount of dose of native type VIP causing a reduction of 15 mmHg in blood pressure shall be made as 100%.

TABLE 2

| Native type VIP | 100 (%) |
|---|---|
| [L-Leu$^{17}$]-VIP-Hse | 21 (%) |
| [L-Leu$^{17}$]-VIP-Hse-NH$_2$ | 54 |
| [L-Leu$^{17}$]-VIP-Hse-NH(CH$_2$)$_9$CH$_3$ | 68 |

As apparently seen from the Table, the VIP analogues show far excellent hypotensing action than the native type VIP.

PHARMACOLOGICAL TEST EXAMPLE 4

(Accelerating Action on Sexual Function)

After exenterating testiculus of male rats (mean body weight: about 250 g) to castrate the same, testosterone (0.4 μg/kg) was continuously injected to each animal for a period of 16 days.

An external cream (prepared by Medicine Preparation Example 10) was applied to a genital organ of each castrated animal (10 μ g/animal as [L-Leu$^{17}$]-VIP-Hse-NH$_2$) and each experimental animal was lived in a cage with a female rat she has sexual acceptability, to check and record a number of times of copulation, over a period of 15 minutes.

As to another external cream consisting of [L-Leu$^{17}$]-VIP-Hse-NH$_2$ and white petrolatum, a test similar to the above was carried out.

Results are shown in following Table 3.

TABLE 3

| Animal | Control | Test Group A | Test Group B |
|---|---|---|---|
| No. 1 | 9 | 13 | 21 |
| 2 | 6 | 12 | 14 |
| 3 | 3 | 16 | 15 |
| 4 | 7 | 11 | 10 |
| 5 | — | 10 | 13 |
| 6 | 10 | 14 | 17 |

In the Table,
Control: Group applied a cream consisting of white petrolatum only;
Test Group A: Group applied the cream consisting of [L-Leu$^{17}$]-VIP-Hse-NH$_2$ and white petrolatum; and
Test Group B: Group applied the cream consisting of [L-Leu$^{17}$]-VIP-Hse-NH$_2$, tannic acid and white petrolatum.

In the Table,
Control: Group applied a cream consisting of white petrolatum only;
Test Group A: Group applied the cream consisting of [L-Leu$^{17}$]-VIP-Hse-NH$_2$ and white petrolatum; and
Test Group B: Group applied the cream consisting of [L-Leu$^{17}$]-VIP-Hse-NH$_2$, tannic acid and white petrolatum.

The result given in the Table shows facts that the VIP analogues strengthen the sexual function, and that the tannic acid provides a rapid or immediate action in some extent.

PHARMACOLOGICAL TEST EXAMPLE 5

(Influence on Growth of Hair)

Hairs on back of each rabbits (mean body weight: about 2.5 kg) were cut with an electric hair-clipper and the cut area was shaved. The experimental animals were classified into 6 groups (5 heads for each group). The shaved area was divided into 4 sections. A control solution (aqueous solution of saponin, which contains the saponin in a ratio of 50 mg to 5 ml of water) was applied on the 2 sections and a test solution selected from the followings was applied on remaining 2 sections by an amount of about 0.2 ml/day for each section with an area of 9 cm$^2$, for a period of 4 weeks.

TEST SOLUTIONS

A: Aqueous solution according to Medicine Preparation Example 4 and containing [L-Leu$^{17}$]-VIP-Hse-NH(CH$_2$)$_9$CH$_3$ and saponin, B: Aqueous solution with a similar prescription to the Solution A excepting that the VIP analogue is [L-Leu$^{17}$]-VIP-Hse, C: Aqueous solution with a similar prescription to the Solution A excepting that the VIP analogue is [L-Leu$^{17}$]-VIP-Hse-NH$_2$, D: Aqueous solution of [L-Leu$^{17}$]-VIP-Hse-NH(CH$_2$)$_9$CH$_2$, which contains the VIP analogue in a ratio of 5 mg to water of 5 ml, E: Aqueous solution of [L-Leu$^{17}$]-VIP-Hse, which contains the VIP analogue in a ratio of 5 mg to water of 5 ml, and F: Aqueous solution of [L-Leu$^{17}$]-VIP-Hse-NH$_2$, which contains the VIP analogue in a ratio of 5 mg to water of 5 ml.

On the day after the final application, an accelerating action of hair growth was evaluated under following standards for the judgement.

STANDARDS FOR JUDGEMENT

Score, 2 points:
Acceleration of hair growth was recognized in 5 mm or more, in comparison with hairs in the sections where the control solution was applied, Score, 1 point:
Acceleration of hair growth was recognized in less than 5 mm, in comparison with hairs in the sections where the control solution was applied, and Score, 1 (zero) point:
No acceleration of hair growth was recognized, in comparison with hairs in the sections where the control solution was applied.

Results are shown in following Table 4.

TABLE 4

| Test Solutions | Sum of scores |
|---|---|
| A | 9 |
| B | 10 |
| C | 8 |
| D | 4 |
| E | 6 |
| F | 3 |

It is apparent from the Table that each of the VIP analogues according to the invention shows an acceleration of hair growth, and that the coexistence of saponin increases the acceleration.

PHARMACOLOGICAL TEST EXAMPLE 6

(Inhibition of Contraction in Respiratory Tract)

An inhibition of contraction in respiratory tract, which shall be caused by an inhalation of VIP analogues as Test samples, was checked with use of a guinea pig model of respiratory tract contraction to be induced with an ascaris.

The experimental animals (mean body weight: about 500 g) sensitized with the ascaris were classified into following 4 groups (3 heads for each group).

CONTROL GROUP

Inhalant: Saline (3 ml),

TEST GROUP A

Inhalant: Saline of a dry powder obtained by Medicine Preparation Example 1, which contains [L-Leu$^{17}$]-VIP-Hse-NH$_2$ of 1 mg/3 ml,

TEST GROUP B

Inhalant: Saline similar to that for Test Group A, excepting that the VIP analogue is [L-Leu$^{17}$]-VIP-Hse, and

TEST GROUP C

Inhalant: Saline solution similar to that for Test Group A, excepting that the VIP analogue is [L-Leu$^{17}$]-VIP-Hse-NH(CH$_2$)$_9$CH$_3$.

After giving the inhaltant for a period of 5 minutes to each of the experimental animals in the groups, an ascaris solution (20 mg/3 ml) was given for a period of 3 minutes with use of an inhaler. Measurements of a respiratory resistance and a dynamic compliance, as indexes of the contraction of respiratory tract were carried out by 7 times, namely just before the inhalation of the ascaris solution, just after the inhalation, and each period of time after 10, 20, 30, 45 and 60 minutes from the inhalation.

Influences of the inhalants for Test Groups to the respiratory resistance and dynamic compliance are given in following Tables 5 and 6 with relative values, when values at just after the inhalation of ascaris solution, and each period of time after 10, 30 and 60 minutes from the inhalation, on the Control Group shall be made as 100%.

TABLE 5

| | (Respiratory Resistance) | | | |
|---|---|---|---|---|
| | Control Group | Test Group A | Test Group B | Test Group C |
| Just after inhalation | 100% | 62% | 59% | 67% |
| After 10 min. | 100% | 65% | 53% | 72% |
| After 30 min. | 100% | 72% | 69% | 80% |
| After 60 min. | 100% | 81% | 78% | 86% |

TABLE 6

| | (Dynamic Compliance) | | | |
|---|---|---|---|---|
| | Control Group | Test Group A | Test Group B | Test Group C |
| Just after inhalation | 100% | 135% | 140% | 132% |
| After 10 min. | 100% | 134% | 141% | 128% |
| After 30 min. | 100% | 136% | 139% | 123% |
| After 60 min. | 100% | 131% | 138% | 115% |

What is claimed is:

---

SEQUENCE LISTING ( 1 ) GENERAL INFORMATION:

( i i i ) NUMBER OF SEQUENCES: 3

( 2 ) INFORMATION FOR SEQ ID NO:1:

( i ) SEQUENCE CHARACTERISTICS:
        ( A ) LENGTH: 28 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:1:

```
His Ser Asp Ala Val Phe Thr Asp Asn Tyr Thr Arg Leu Arg Lys Gln
 1               5                  10                  15
Met Ala Val Lys Lys Tyr Leu Asn Ser Ile Leu Asn
                20                  25
```

( 2 ) INFORMATION FOR SEQ ID NO:2:

( i ) SEQUENCE CHARACTERISTICS:
        ( A ) LENGTH: 29 amino acids
        ( B ) TYPE: amino acid
        ( D ) TOPOLOGY: linear ( i i ) MOLECULE TYPE: peptide ( i x ) FEATURE:
        ( A ) NAME/KEY: Peptide
        ( B ) LOCATION: 17
        ( D ) OTHER INFORMATION: /note="Xaa is a residue of an amino
            acid other than methionine (met)"

( i x ) FEATURE:
        ( A ) NAME/KEY: Peptide
        ( B ) LOCATION: 29
        ( D ) OTHER INFORMATION: /note="Xaa is homoserine,
            homoserine- lactone, amidized homoserine, a residue
            reacted homoserine-lactone with a primary alkyl amine
            having carbon atoms not exceeding 20, or an optional
            polypeptide chain containing an amidized homoserine at
            the C- terminal"

( x i ) SEQUENCE DESCRIPTION: SEQ ID NO:2:

```
His Ser Asp Ala Val Phe Thr Asp Asn Tyr Thr Arg Leu Arg Lys Gln
1               5               10                      15

Xaa Ala Val Lys Lys Tyr Leu Asn Ser Ile Leu Asn Xaa
            20                  25
```

( 2 ) INFORMATION FOR SEQ ID NO:3:

( i ) SEQUENCE CHARACTERISTICS:
        ( A ) LENGTH: 29 amino acids
        ( B ) TYPE: amino acid
        ( D ) TOPOLOGY: linear ( i i ) MOLECULE TYPE: peptide ( i x ) FEATURE:
        ( A ) NAME/KEY: Peptide
        ( B ) LOCATION: 29
        ( D ) OTHER INFORMATION: /note="Xaa is a homoserine or
        homoserine- lactone residue"

( x i ) SEQUENCE DESCRIPTION: SEQ ID NO:3:

```
His Ser Asp Ala Val Phe Thr Asp Asn Tyr Thr Arg Leu Arg Lys Gln
1               5               10                      15

Leu Ala Val Lys Lys Tyr Leu Asn Ser Ile Leu Asn Xaa
            20                  25
```

1. A method for treating asthma comprising administering to a patient in need of such treatment an effective amount of a pharmaceutical composition comprising an amount of a vasoactive intestinal polypeptide (VIP) analogue (SEQ ID NO: 2) selected from the group consisting of [L-Leu$^{17}$]-VIP-Hse, [L-Leu$^{17}$]-VIP-Hse-NH$_2$, [L-Leu$^{17}$]-VIP-Hse-NH(CH$_2$)$_9$CH$_3$, [L-Leu$^{17}$]-VIP-Hse-NH(CH$_2$)$_{19}$CH$_3$ and a pharmaceutically acceptable salt thereof, effective to treat asthma, in combination with a surfactant and a pharmaceutically acceptable carrier.

2. A method for treating hyperpiesia comprising administering to a patient in need of such treatment an effective amount of a pharmaceutical composition comprising an amount of a vasoactive intestinal polypeptide (VIP) analogue (SEQ ID NO: 2) selected from the group consisting of [L-Leu$^{17}$]-VIP-Hse, [L-Leu$^{17}$]-VIP-Hse-NH$_2$, [L-Leu$^{17}$]-VIP-Hse-NH(CH$_2$)$_9$CH$_3$, [L-Leu$^{17}$]-VIP-Hse-NH(CH$_2$)$_{19}$CH$_3$ and a pharmaceutically acceptable salt thereof, effective to treat hyperpiesia, in combination with a surfactant and a pharmaceutically acceptable carrier.

3. A method for treating impotence comprising administering to a patient in need of such treatment an effective amount of a pharmaceutical composition comprising an amount of a vasoactive intestinal polypeptide (VIP) analogue (SEQ ID NO: 2) selected from the group consisting of [L-Leu$^{17}$]-VIP-Hse, [L-Leu$^{17}$]-VIP-Hse-NH$_2$, [L-Leu$^{17}$]-VIP-Hse-NH(CH$_2$)$_9$CH$_3$, [L-Leu$^{17}$]-VIP-Hse-NH(CH$_2$)$_{19}$CH$_3$ and a pharmaceutically acceptable salt thereof, effective to treat impotence, in combination with a surfactant and a pharmaceutically acceptable carrier.

4. A method for treating anaphylaxis comprising administering to a patient in need of such treatment an effective amount of a pharmaceutical composition comprising an amount of a vasoactive intestinal polypeptide (VIP) analogue (SEQ ID NO: 2) selected from the group consisting of [L-Leu$^{17}$]-VIP-Hse, [L-Leu$^{17}$]-VIP-Hse-NH$_2$, [L-Leu$^{17}$]-VIP-Hse-NH(CH$_2$)$_9$CH$_3$, [L-Leu$^{17}$]-VIP-Hse-NH(CH$_2$)$_{19}$CH$_3$ and a pharmaceutically acceptable salt thereof, effective to treat anaphylaxis, in combination with a surfactant and a pharmaceutically acceptable carrier.

5. A pharmaceutical composition suitable for the treatment of asthma, hyperpiesia, impotence and accelerating secretions of the lachrymal gland, comprising an effective amount of a vasoactive intestinal polypeptide (VIP) analogue (SEQ ID NO: 2) selected from the group consisting of [L-Leu$^{17}$]-VIP-Hse, [L-Leu$^{17}$]-VIP-Hse-NH$_2$, [L-Leu$^{17}$]-VIP-Hse-NH(CH$_2$)$_9$CH$_3$, [L-Leu$^{17}$]-VIP-Hse-NH(CH$_2$)$_{19}$CH$_3$ and a pharmaceutically acceptable salt thereof, in combination with a surfactant and a pharmaceutically acceptable carrier.

6. A pharmaceutical composition according to claim 5, wherein said surfactant is selected from the group consisting of tannic acid or a salt thereof, saponin and a polyoxyethylene higher alcohol ether.

7. A pharmaceutical composition according to claim 5, further comprising a peptidase inhibitor.

8. A pharmaceutical composition according to claim 7, wherein said peptidase inhibitor is selected from the group consisting of trypsin inhibitor, chymotrypsin inhibitor, gavexate, guanidinobenzoic acid and an acidic polysaccharide.

* * * * *